United States Patent [19]

Sherts

[11] Patent Number: 5,511,410

[45] Date of Patent: Apr. 30, 1996

[54] RESILIENCY TESTING DEVICE FOR TENNIS BALLS

[76] Inventor: Charlie R. Sherts, 70 Washington St., #302, Norwalk, Conn. 06854

[21] Appl. No.: 321,810

[22] Filed: Oct. 12, 1994

[51] Int. Cl.6 .................................................. G01N 3/48
[52] U.S. Cl. ............................................................ 73/81
[58] Field of Search .................................. 73/81, 82, 85, 73/81 B

[56] References Cited

U.S. PATENT DOCUMENTS

| | | | |
|---|---|---|---|
| 2,278,416 | 4/1942 | Ahi | 73/818 |
| 2,628,496 | 2/1953 | Wick | 73/818 |
| 3,470,737 | 10/1969 | Fridley | 73/81 |
| 4,136,554 | 1/1979 | Larson | 73/81 |
| 5,222,391 | 6/1993 | Reenstra | 73/81 |
| 5,372,030 | 12/1994 | Prussia et al. | 73/81 |

*Primary Examiner*—Robert Raevis
*Attorney, Agent, or Firm*—Handal & Morofsky

[57] ABSTRACT

A sports ball resiliency testing device is disclosed. The device includes a housing that defines a receiving area into which a ball is placed. The receiving area is configured and dimensioned to act upon the contours of the ball. A movable member extends into the receiving area and makes contact with the surface of the ball. The movable member is urged by a spring so as to exert a compressing force on the ball. The urging force of the spring is adjustable so as to provide for various testing ranges. The ball thus exerts a resisting force against the movable member. A value of the resisting force is determined when an equilibrium is reached between the compressing force and the resisting force. This value indicates the playability of the ball.

21 Claims, 5 Drawing Sheets

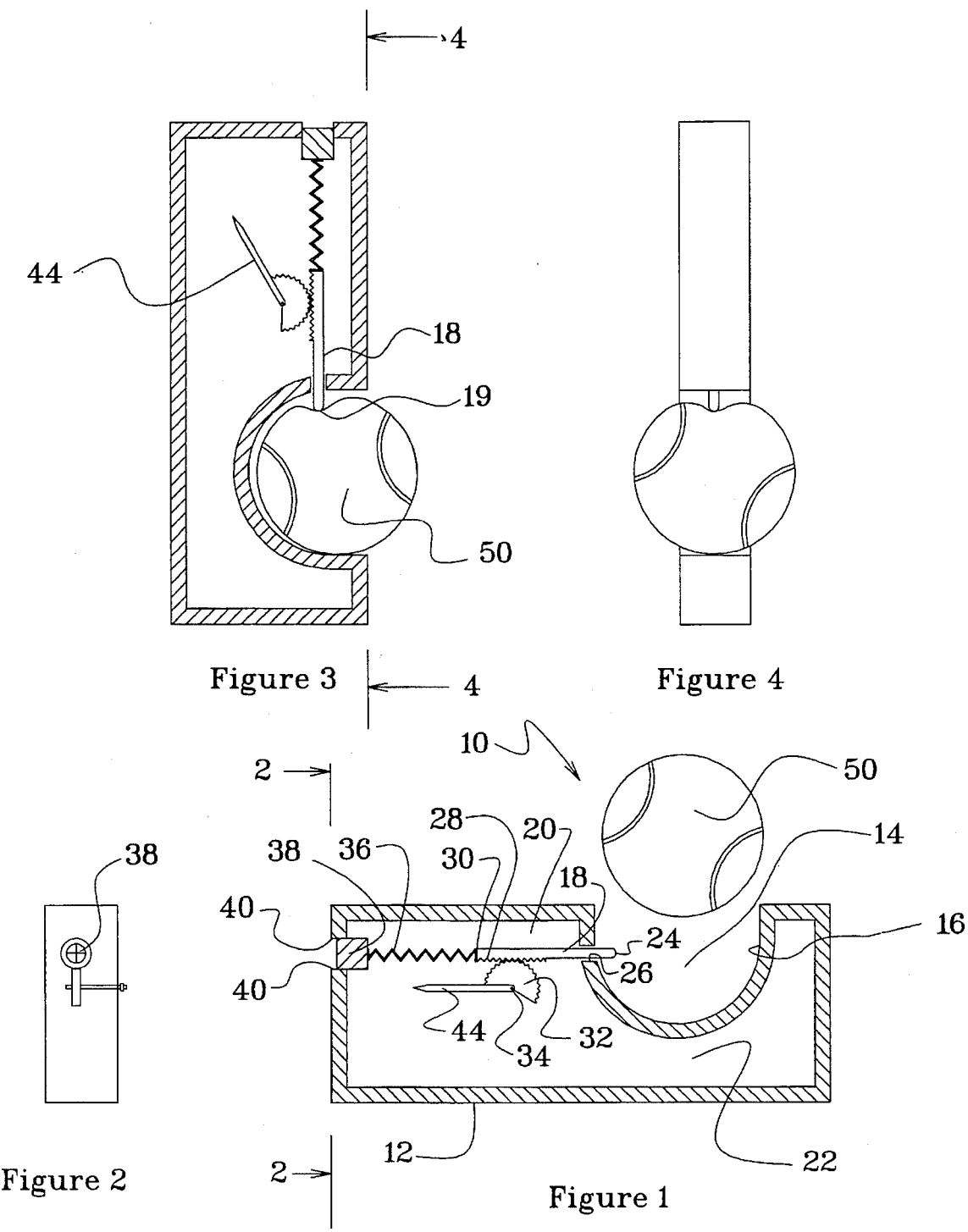

5,511,410

RESILIENCY TESTING DEVICE FOR TENNIS BALLS

TECHNICAL FIELD

The present invention relates to a portable device for testing the resiliency of tennis balls and other types of balls used in athletic games.

BACKGROUND

One of today's most popular recreational and professional sports is tennis. Interest in tennis is not limited to the U.S. but extends very nearly to the entire world. The sport of tennis has its origins hundreds of years ago and most sports fans have heard of the Wimbledon tournament which is nearly as old as the sport itself.

Naturally, the rules and regulations of the sport have been clearly defined. For instance, a tennis ball intended for professional use must be inflated to precise specifications during manufacture. However, once shipped from the factory, some tennis balls may lose some of their resiliency and become defective. Once in the hands of the user the only way to test for these deficiencies is by a rudimentary test of bouncing the ball on the playing surface or by squeezing it, neither of which is very accurate. The present invention is concerned with this problem. More particularly, the present invention is concerned with a manner in which a player can quickly and efficiently determine whether or not a ball is suitable for play.

As might be expected, there is no shortage of devices for testing the compressibility of a ball. For example, U.S. Pat. No. 3,665,757, issued to Hoag, discloses a device for checking the concentricity and compression of a golf ball. Hoag utilizes a lever for exerting a force upon the golf ball, forcing the golf ball against a spring gauge to measure the compressibility of the golf ball. See also U.S. Pat. No. 2,278,416, issued to Atti, which discloses a similar device.

U.S. Pat. No. 2,628,496, issued to Wick, discloses a portable golf ball tester. This device is similar to those disclosed in the above-mentioned references except for the manner in which force is exerted upon the ball. In Wick, the force is exerted upon the surface of the golf ball by a screw which when tightened increases the force exerted upon the ball being tested.

However, none of the above patents discloses a portable device which provides the user with a quick and efficient means to determine whether a ball is suitable for play. U.S. Pat. No. 5,222,391 issued to Reenstra discloses a device which attempts to address these deficiencies. Reenstra discloses a device which compresses a tennis ball to a predetermined size. This predetermined size is the maximum allowable for a tennis ball that is suitable for play when placed under an eighteen pound load. This device incorporates an electronic sensor that determines whether eighteen pounds of pressure was used to deform the ball.

However, Reenstra does not indicate how much pressure is actually being used, the device only indicates if eighteen pounds of pressure was used to deform the ball. Also, the device housing in Reenstra is strictly designed to test tennis-sized balls only, there is no allowance for adaptability to test other types of balls. In addition, Reenstra relies on an electronic sensor that is subject to failure and may be susceptible to environmental conditions encountered on the court.

SUMMARY OF THE INVENTION

The invention, as claimed, is intended to provide a remedy. It solves the problem of how to quickly determine the condition of a sports ball. The invention contemplates a novel idea for greatly reducing the incidence of improperly discarded sports balls. An object of the invention is to provide a testing device for different types of sports balls that is relatively inexpensive to produce, easy to use and provides a high degree of accuracy.

The present invention can be set at predetermined testing parameters so that a user can select the appropriate range required. This allows the user to simply place the ball in the device and determine its compressibility according to the predetermined range.

The present invention is also designed to be able to incorporate balls of different dimensions. The invention can be equipped with a hinged receiving area that allows the receiving area of the device to vary in size.

BRIEF DESCRIPTION OF THE DRAWINGS

FIG. 1 is a cross sectional side view of an embodiment of a sports ball testing device constructed in accordance with the present invention;

FIG. 2 is a cross sectional view along the lines 2—2 of FIG. 1 showing an adjustment structure for a sensing device in accordance with the inventive sports ball testing device illustrated in FIG. 1;

FIG. 3 is a cross sectional side view of the inventive sports ball testing device shown in operation;

FIG. 4 is a view along the lines 4—4 of FIG. 3;

BEST MODE FOR CARRYING OUT THE INVENTION

Figure 7:
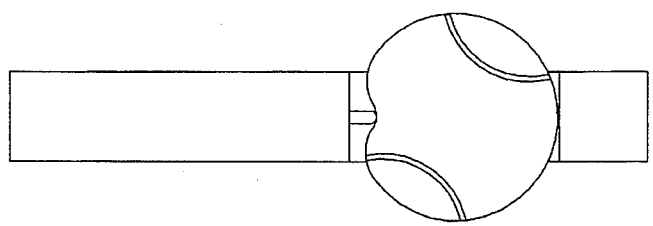
FIG. 7 is a side view along the lines 7—7 of FIG. 6.

Referring to FIG. 1, a sports ball testing device 10 constructed in accordance with the present invention is illustrated. Testing device 10 comprises a testing device housing 12 which houses and supports the other components of testing device 10. Testing device housing 12 can be constructed of a durable material such as plastic which is easily manufactured in a variety of configurations.

As illustrated in FIGS. 1 and 3, a receiving area 14 is defined by the testing device housing 12. During operation of the inventive sports ball testing device 10, receiving area 14 receives and holds a ball 50 to be placed within the receiving area 14. Receiving area 14 constrains a uniform and consistent testing configuration for testing ball 50 to allow accurate and repeatable results. Receiving area 14 is defined between a fixed support surface 16 and a movable member 18. Moveable member 18 is located opposite support surface 16 and extends into the testing end 20 of the housing 12 of receiving area 14. Support surface 16 is maintained in a rigid position by a contoured portion 22 of housing 12. Contoured portion 22 maintains the position of support surface 16 in opposing relationship to moveable member 18.

As ball 50 is placed within receiving area 14 so that a contact end 24 of moveable member 18 and fixed support surface 16 make contact with ball 50.

A spring 36 provides an urging force on the movable member 18 so that a compressing force is exerted on ball 50 at contact point 24. The urging force exerted by spring 36 is adjustable through a calibration screw 38. When turned, calibration screw 38 moves through a threaded hole 40 in housing unit 12.

A middle portion of movable member 18 is equipped with a rack 28 which mates with a pinion 32. Pinion 32 is rotatably supported at its center 34 so that pinion 32 will rotate when sensing stem 18 moves. Pinion 32 is also attached at its center 34 to an indicator dial arm 44. Thus, when pinion 32 rotates it causes indicator dial arm 44 to move. When displaced from its original position, indicator dial arm 44 will show the amount of compressing force exerted on the ball 50 by referencing an indicator dial scale 146 on the surface of the housing 12. This reading when compared to the predetermined testing parameters, will indicate the condition or playability of the ball 50.

The distance between fixed support surface 16 and contact end 24 of extended movable member 18 are significantly smaller than the diameter of ball 50. Thus, when ball 50 is placed within receiving area 14, the portion of ball 50 touching contact end 24 will reach a point of equilibrium 19. The force exerted by compressed ball 50 causes the movable member to slide through a guiding port 26 until the force exerted by the ball 50 equals the urging force exerted by spring 36 on moveable member 18, at which a point of equilibrium is reached.

When tightened, calibration screw 38 compresses spring 36 and thereby increases the force exerted upon movable member 18 at point 30. The compression of spring 36 increases the force required at contact point 24 to displace movable member 18 by the ball 50. This allows the testing device to be calibrated to include higher and lower testing ranges of pressures, by providing different pressures for different types of balls.

As can be seen most clearly in FIGS. 1 and 3, movable member 18 is displaced when ball 50 is placed within receiving area 14. This causes the rack 28 of sensing stem 18 to act upon the pinion 32. When pinion 32 rotates, indicator dial arm 44 moves. The movement of indicator dial arm 44 will indicates the force exerted by ball 50. This indication is then used to determine the playability of the ball 50.

Figure 5:
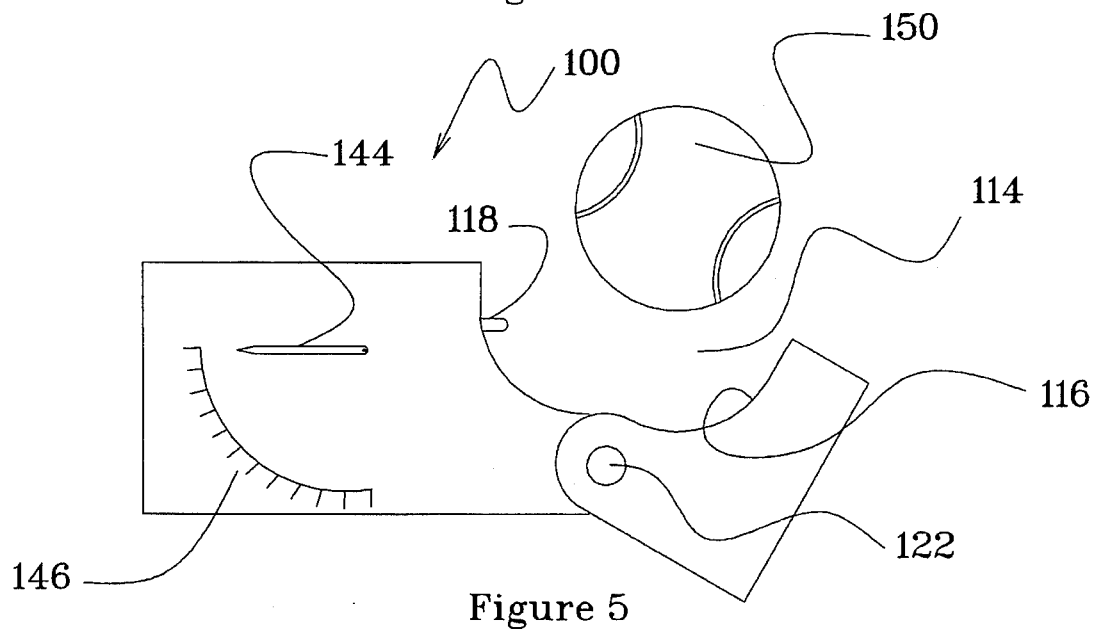
FIG. 5 is a side view of an alternative embodiment of the present invention.

The testing parameters can be predefined by an adjustment to calibration screw 38 as show in FIG. 2. This feature allows for various testing parameters. Once the desired testing range for a particular type of sports ball is defined the inventive device is ready for continuous use. An alternative embodiment is illustrated in FIG. 5. Generally, similar parts or parts performing analogous, corresponding or identical functions to those of the FIG. 1 embodiment are numbered herein with numbers which differ from those of the earlier embodiment by multiples of one hundred.

Figure 6:
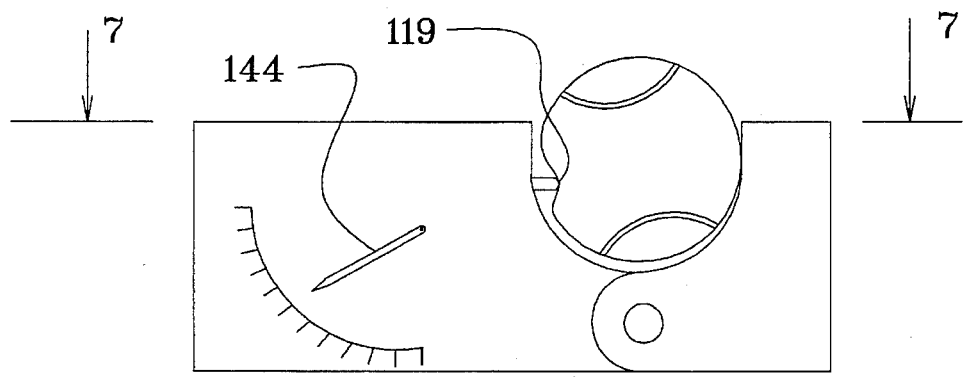
FIG. 6 is a side view of the alternative embodiment of FIG. 5 shown in operation.

Referring in particular to FIG. 5, a ball testing system 100 having certain characteristics in common with the system of the earlier embodiment is illustrated. In this illustration the fixed support surface 116 is appropriately curved to accommodate the surface of ball 150 while being placed in receiving area 114. The location of fixed support surface 116 is adjustable through the incorporation of a hinge 122. Hinge 122 replaces the contoured connecting portion 22 of the earlier embodiment in FIG. 1. This embodiment of the present system 100 allows the receiving area 114 to be adjusted in its size and configuration. This additional feature allows for sports balls of different types and sizes to be tested. FIGS. 5 and 6 also show that when ball 150 is placed within receiving area 114, movable member 118 is displaced by ball 150 to a point of equilibrium 119 causing indicator dial arm 144 to move. When the point of equilibrium 119 is reached between sensing stem 118 and ball 150, indicator dial arm 144 will show the force exerted by ball 150. This force is determined by referencing the indicator dial scale 146 on surface of system 100.

Figure 8:
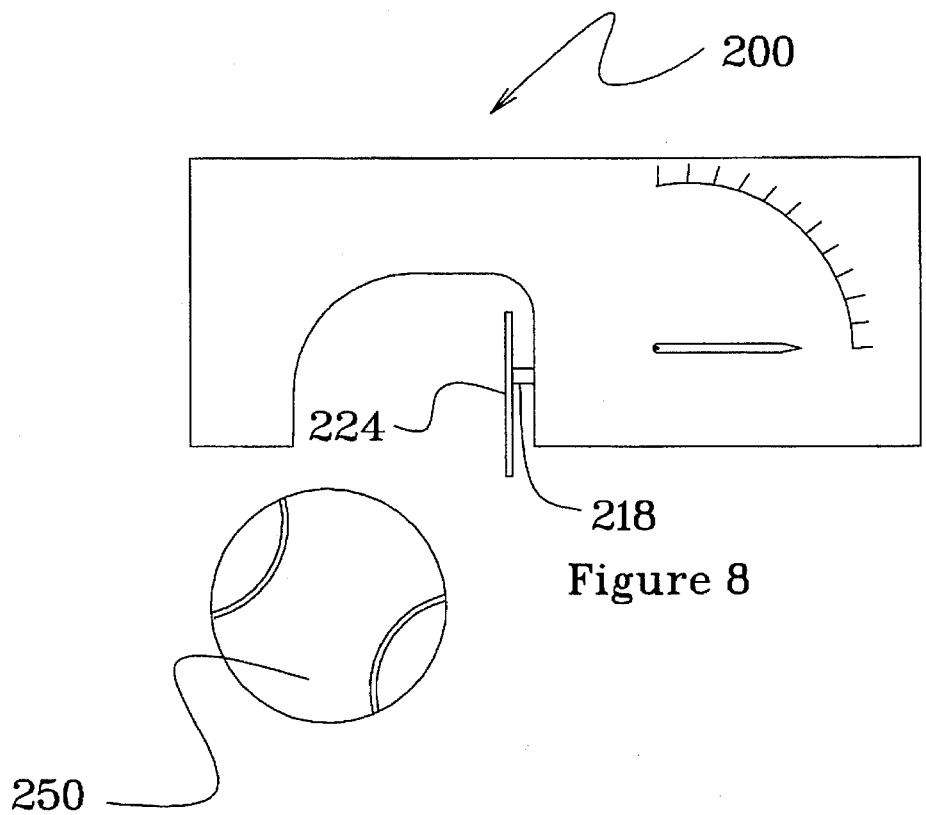
FIG. 8 is a side view of another alternative embodiment of the present invention.
Figure 9:
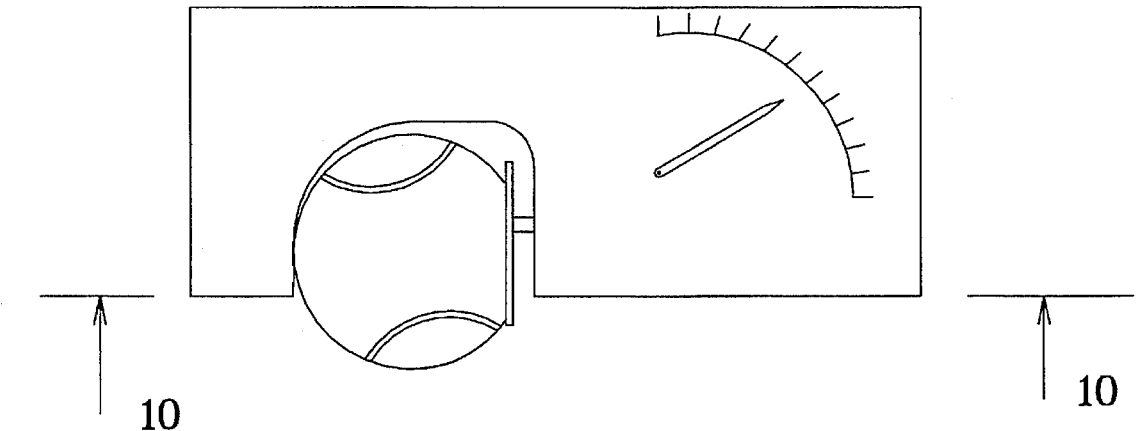
FIG. 9 illustrates the device of FIG. 8 in use.
Figure 10:
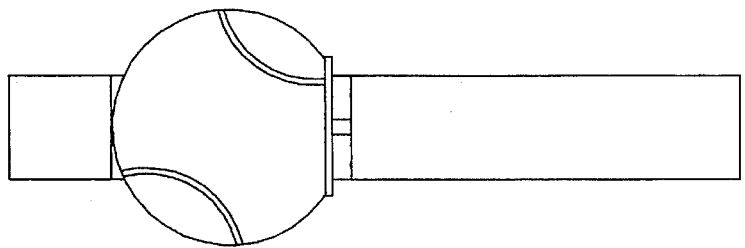
FIG. 10 is a side view along the lines 10—10 of FIG. 9.

Another alternative embodiment is illustrated in FIGS. 8–10. Generally, similar parts or parts performing analogous, corresponding or identical functions to those of the FIG. 1 embodiment are numbered herein with numbers which differ from those of the earlier embodiment by multiples of one hundred. Referring to FIGS. 8–10, a ball testing device 200 having certain characteristics in common with the device of the earlier embodiment is illustrated. Movable member 218 is equipped with a planar surface 224. Planar surface 224 is perpendicularly situated in respect to movable member 218. This feature allows for a larger contact surface that exerts a uniform compressing force upon ball 250. In addition, the larger contact surface of planar surface 224 protects ball 250 from possible damage.

Figure 11:
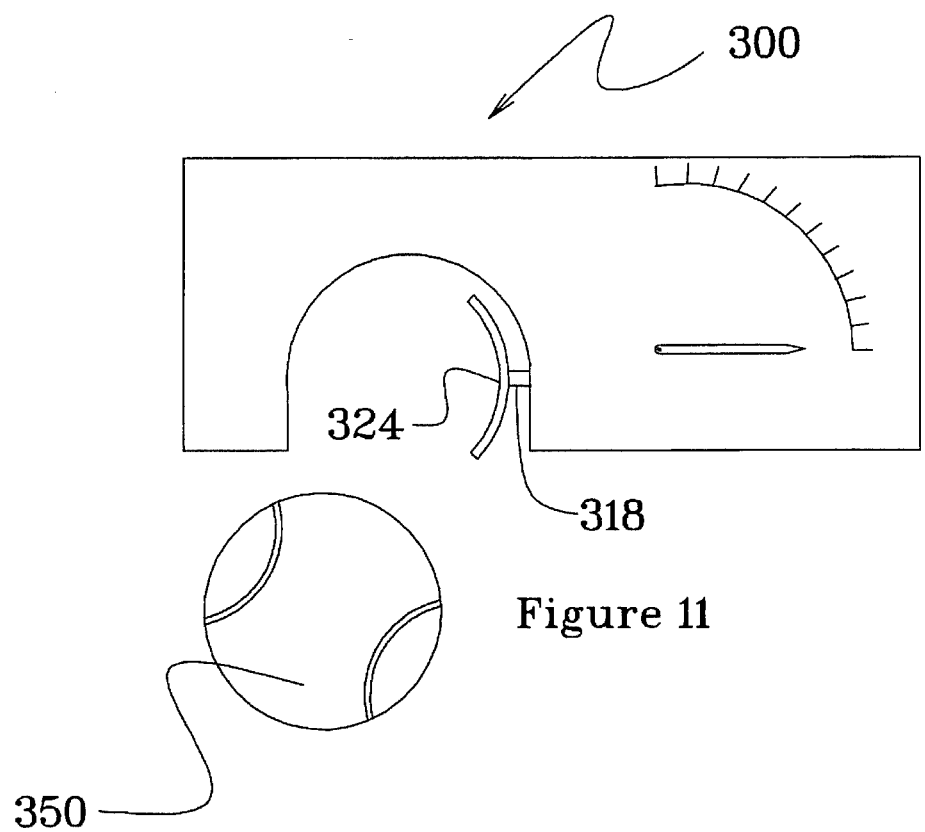
FIG. 11 is a side view of yet another alternative embodiment of the present invention.
Figure 12:
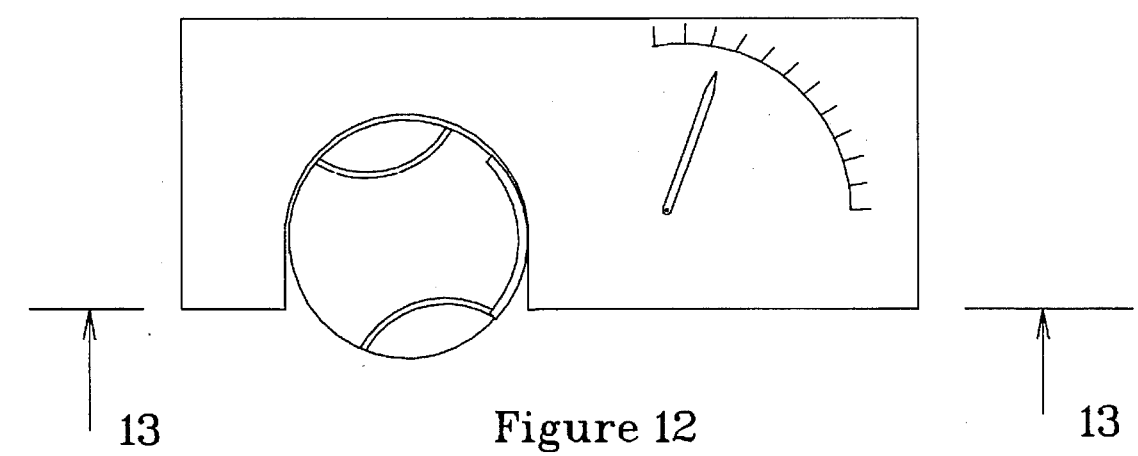
FIG. 12 illustrates the device of FIG. 11 in use.
Figure 13:
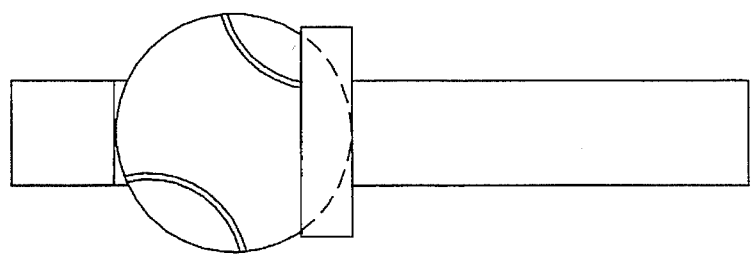
FIG. 13 is a side view along the lines 13—13 of FIG. 12.

Another alternative embodiment is illustrated in FIGS. 11–13. Generally, similar parts or parts performing analogous, corresponding or identical functions to those of the FIG. 1 embodiment are numbered herein with numbers which differ from those of the earlier embodiment by multiples of one hundred.

Referring in particular to FIGS. 11–13, a ball testing device 300 having certain characteristics in common with the device of the earlier embodiment is illustrated. Movable member 318 is equipped with a contoured contact surface 324. Contoured contact surface 324 is perpendicularly situated in respect to movable member 318. This feature allows for a larger contact surface that exerts a uniform compressing force upon ball 350. In addition, the contoured contact surface 324 protects the ball 350 from possible damage.

Figure 14:
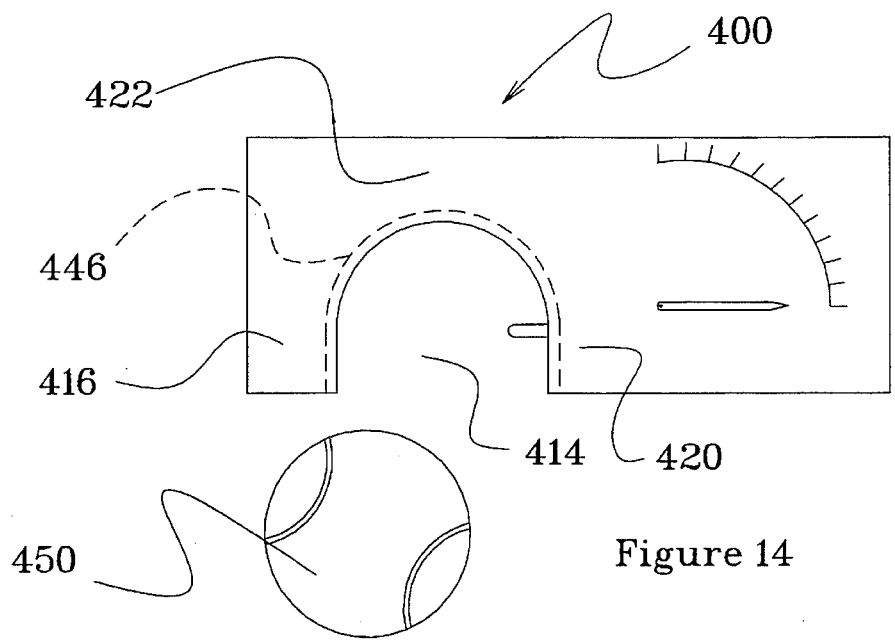
FIG. 14 is a side view of yet another embodiment of the present system.
Figure 15:
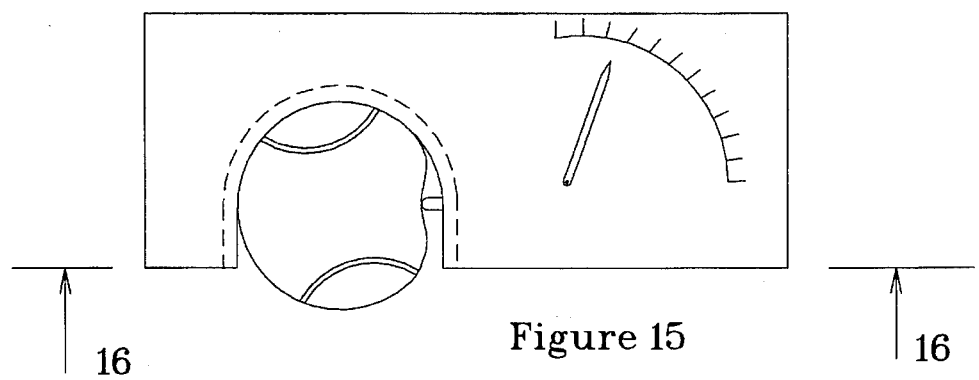
FIG. 15 is an illustration of the FIG. 14 embodiment of the present invention in use.
Figure 16:
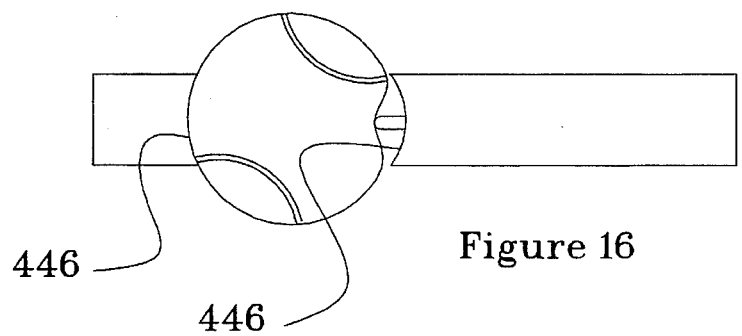
FIG. 16 is a side view along lines 16—16 of FIG. 15.

Another alternative embodiment is illustrated in FIGS. 14–16. Generally, similar parts or parts performing analogous, corresponding or identical functions to those of the FIG. 1 embodiment are numbered herein with numbers which differ from those of the earlier embodiment by multiples of one hundred.

Referring to FIGS. 14–16, a ball testing device 400 having certain characteristics in common with the device of the earlier embodiment is illustrated. The receiving area 414 is equipped with a contoured surface 446 which encompasses the entire receiving area from the fixed support end 416 to the contoured connecting portion 422 and to the testing end 420. As can be seen most clearly in FIG. 16 the contoured surface 446 is configured and dimensioned in accordance to the exterior curvature of the ball 450. Contoured surface 446 protects the surface of the ball 450 from damage while maintaining a uniform support on the exterior surface of the ball.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. A sports ball testing device, comprising:
   (a) a housing defining a receiving area for receiving a ball to be tested;
   (b) a moveable member extending into said receiving area for contacting and exerting a compressing force on said ball against a resisting force exerted by said ball;
   (c) urging means for exerting an urging force on said moveable member in a direction effective for urging said moveable member to exert the compressing force on said ball;
   (d) adjusting means for adjusting the urging force exerted by said urging means so as to provide for various testing ranges;
   (e) indicating means coupled to said urging means for indicating the value of the resisting force in response to the physical configuration of said urging means when the equilibrium is reached between the compressing force and the resisting force.

2. A sports ball tester as in claim 1, wherein said housing includes a hinged portion defining said receiving area so that said receiving area is adjustable in its size and configuration to allow for different size balls to be tested.

3. A sports ball tester as in claim 1, wherein said housing includes means for adjusting the size of said receiving area to allow for different size balls to be tested.

4. A sports ball tester as in claim 2, further comprising a contoured contact surface attached perpendicularly to said movable member to provide a large contacting surface.

5. A sports ball tester as in claim 2, wherein said indicating means includes an indicating arm for providing an incremental readout against a scale on said housing of the value of the resisting force.

6. A sports ball tester as in claim 2, wherein said housing includes a fixed end defining said receiving area and having a curved surface for accommodating said ball.

7. A sports ball tester as in claim 2, wherein said receiving area is configured and dimensioned throughout to resemble the curative of said ball.

8. A sports ball tester device according to claim 1, wherein said urging means urges said moveable member toward a supporting surface portion of said receiving area opposite said urging means and comprising a portion of said receiving area defined by said housing.

9. A sports ball tester as in claim 1, wherein said indicating means is coupled to said urging member by a rack and pinion.

10. A sports ball tester as in claim 1, wherein said housing includes means for adjusting the size of said receiving area to allow for different size balls to be tested.

11. A sports ball tester as in claim 1, further comprising a planar contact surface attached perpendicularly to said moveable member to provide a large contact surface.

12. A sports ball tester as in claim 1, further comprising a contoured contact surface attached perpendicularly to said moveable member to provide a large contacting surface.

13. A sports ball tester as in claim 1, wherein said indicating means includes an indicating member for providing an incremental readout of the value of the resisting force and a scale proximate which said indicator member moves, said indicator member being coupled to said urging means and said scale being attached to said housing.

14. A sports ball tester as in claim 1, wherein said housing includes a fixed end defining said receiving area and having curved surface for accommodating said ball.

15. A sports ball testing device, comprising:
   (a) a housing defining a receiving area for receiving a ball to be tested;
   (b) a housing member extending into said receiving area for contacting and exerting a compressing force on said ball against a resisting force exerted by said ball, said resisting force being dependent on playability of said ball;
   (c) urging means for exerting an urging force on said moveable member in a direction effective for urging said moveable member to exert said compressing force on said ball, said urging force having a testing range specific for a particular ball type;
   (d) adjusting means for adjusting the testing range of the urging force exerted on said moving member to provide a plurality of testing ranges for testing different types of balls;
   (e) determining means for determining a value of said resisting force exerted by said ball when an equilibrium is reached between the compressing force and the resisting force; and
   (f) indicating means for indicating the value of the resisting force when the equilibrium is reached so as to indicate the playability of said ball.

16. A sports ball testing device according to claim 15, wherein said housing includes means for altering said receiving area so that said receiving area is effective to accommodate balls of different sizes to be tested.

17. A sports ball testing device according to claim 15, wherein said housing includes a hinged portion defining said receiving area so that said receiving area is adjustable in its size and configuration to accommodate balls of different sizes to be tested.

18. A sports ball testing device according to claim 15, further comprising a planar contacting member attached to said moveable member for providing a large contacting surface.

19. A sports ball testing device according to claim 15, further comprising a contoured contacting member attached to said moveable member for providing a large contacting surface.

20. A sports ball testing device according to claim 15, wherein said indicating means includes an indicating arm positionable depending on said value.

21. A sports ball testing device according to claim 15, wherein said housing includes a fixed end defining said receiving area and having a curved surface for accommodating said ball.

* * * * *